United States Patent
Maurer et al.

(10) Patent No.: US 7,088,230 B2
(45) Date of Patent: *Aug. 8, 2006

(54) CHEMICAL, BIOLOGICAL, RADIOLOGICAL, AND NUCLEAR WEAPON DETECTION SYSTEM WITH ALARM THRESHOLDS BASED ON ENVIRONMENTAL FACTORS

(75) Inventors: Scott M. Maurer, Haymarket, VA (US); Mark J. Derksen, Bristow, VA (US); Kevin J. Kofler, Bristow, VA (US); Robert H. Fleming, Manassas, VA (US)

(73) Assignee: Lockheed Martin Corporation, Bethesda, MD (US)

( * ) Notice: Subject to any disclaimer, the term of this patent is extended or adjusted under 35 U.S.C. 154(b) by 132 days.

This patent is subject to a terminal disclaimer.

(21) Appl. No.: 10/881,995

(22) Filed: Jun. 30, 2004

(65) Prior Publication Data

US 2006/0001536 A1    Jan. 5, 2006

(51) Int. Cl.
*G08B 29/00* (2006.01)
(52) U.S. Cl. .................... 340/511; 340/522
(58) Field of Classification Search ........... 340/511, 340/539.22, 539.26, 539.28, 521, 522
See application file for complete search history.

(56) References Cited

U.S. PATENT DOCUMENTS

| | | | |
|---|---|---|---|
| 6,710,711 B1 * | 3/2004 | Berry | 340/540 |
| 6,710,715 B1 * | 3/2004 | Deeds | 340/601 |
| 6,897,774 B1 * | 5/2005 | Costa et al. | 340/522 |
| 6,930,596 B1 * | 8/2005 | Kulesz et al. | 340/506 |
| 6,943,684 B1 * | 9/2005 | Berry | 340/540 |
| 6,956,473 B1 * | 10/2005 | Hanood | 340/522 |

* cited by examiner

*Primary Examiner*—John Tweel, Jr.
(74) *Attorney, Agent, or Firm*—DeMont & Breyer LLC

(57) ABSTRACT

A chemical, biological, radiological, and nuclear weapon detection system is disclosed that incorporates a mechanism to reduce the probability that a false alarm will be issued. In particular, the mechanism causes an alarm to be triggered when the amount of a hazardous material reaches a threshold, but changes the threshold based, at least in part, on environmental (e.g., meteorological, etc.) characteristics (e.g., whether is it precipitating or not, whether it is sunny or not, etc) that effect the efficacy of a chemical, biological, radiological, or nuclear weapon. Given that there are environmental factors that make an attack less effective, and given that terrorists are aware of this, the illustrative embodiment is less likely to issue an alarm when the environmental factors suggest that an attack is less effective, and, therefore, less likely. The illustrative embodiment accomplishes this by changing the threshold needed to issue an alarm based on one or more the environmental factors.

22 Claims, 11 Drawing Sheets

Figure 11

VX Gas Alarm Threshold (ppm)

- Sunny and Precipitating
- Night and Precipitating
- Sunny and Not Precipitating
- Not Sunny and Not Precipitating

CHEMICAL, BIOLOGICAL, RADIOLOGICAL, AND NUCLEAR WEAPON DETECTION SYSTEM WITH ALARM THRESHOLDS BASED ON ENVIRONMENTAL FACTORS

FIELD OF THE INVENTION

The present invention relates to civil defense in general, and, more particularly, to chemical, biological, radiological, and nuclear weapons detection systems.

BACKGROUND OF THE INVENTION

A chemical, biological, radiological, or nuclear attack on a civilian population is a dreadful event, and the best response requires the earliest possible detection of the attack so that individuals can flee and civil defense authorities can contain its effects. To this end, chemical, biological, radiological, and nuclear weapons detection systems are being deployed in many urban centers that will give civil defense authorities almost instant notification that an attack has occurred.

SUMMARY OF THE INVENTION

A terrorist seeks to impose his or her will on a government by convincing its citizenry that conciliation—and not confrontation—will make the threat disappear. If the government is able to protect its citizens from violence, the policy of confrontation will be deemed successful and the terrorist's agenda will be thwarted. In contrast, if the terrorist is able to strike wherever and whenever it desires, the policy of confrontation will be deemed unsuccessful and the terrorist's agenda will be promoted by those who favor conciliation.

In either case, the government and the terrorist are locked in a struggle to undermine the citizenry's respect and confidence in the other. It warrants repeating that the salient traits that the government and the terrorists vie for are respect and confidence, and, therefore, any factor—however apparently remote—that enhances or detracts either's respect and confidence is important.

One way that the government earns and maintains the respect and confidence of the citizenry is by quickly and accurately informing the public when an attack has occurred and by taking the appropriate action. This means that there are two ways in which the government can lose the respect and confidence of the citizenry. First, the government can fail to inform the public when an actual attack has occurred, and second, the government can inform the public that an attack has occurred when in fact there has been no such attack. Therefore, it's important for the government to inform the public of an attack when an attack has in fact occurred, but that it is also important for the government not to issue false alarms. To this end, the respect in the government is best enhanced by a chemical, biological, radiological, and nuclear weapon detection system that both: (1) quickly issues an alarm in the event of a real attack, and (2) accurately withholds false alarms.

The illustrative embodiment of the present invention incorporates a mechanism to reduce the probability that a false alarm will be issued. In particular, the mechanism causes an alarm to be triggered when the amount of a hazardous material reaches a threshold, but changes the threshold based, at least in part, on environmental (e.g., meteorological, etc.) characteristics (e.g., whether is it precipitating or not, whether it is sunny or not, etc) that effect the efficacy of a chemical, biological, radiological, or nuclear weapon. For example, it is well understood that a chemical gas attack is likely to be less effective when it is raining than when it is clear because the rain will suppress and dilute the chemical agent.

Given that there are environmental factors that make an attack less effective, and given that terrorists are aware of this, the illustrative embodiment is less likely to issue an alarm when the environmental factors suggest that an attack is less effective, and, therefore, less likely. The illustrative embodiment accomplishes this by changing the threshold needed to issue an alarm based on one or more the environmental factors.

The illustrative embodiment comprises: a first environmental sensor for monitoring a first environmental characteristic; a first hazardous material sensor for measuring the amount of a first hazardous material; and a first alarm that is issued when the amount of the first hazardous material reaches a first threshold, wherein the first threshold changes and is based on the first environmental characteristic.

BRIEF DESCRIPTION OF THE DRAWINGS

FIG. 11 depicts the threshold for VX Gas in parts per million (ppm) as a function of both precipitation and whether or not it is sunny.

DETAILED DESCRIPTION

Figure 1:
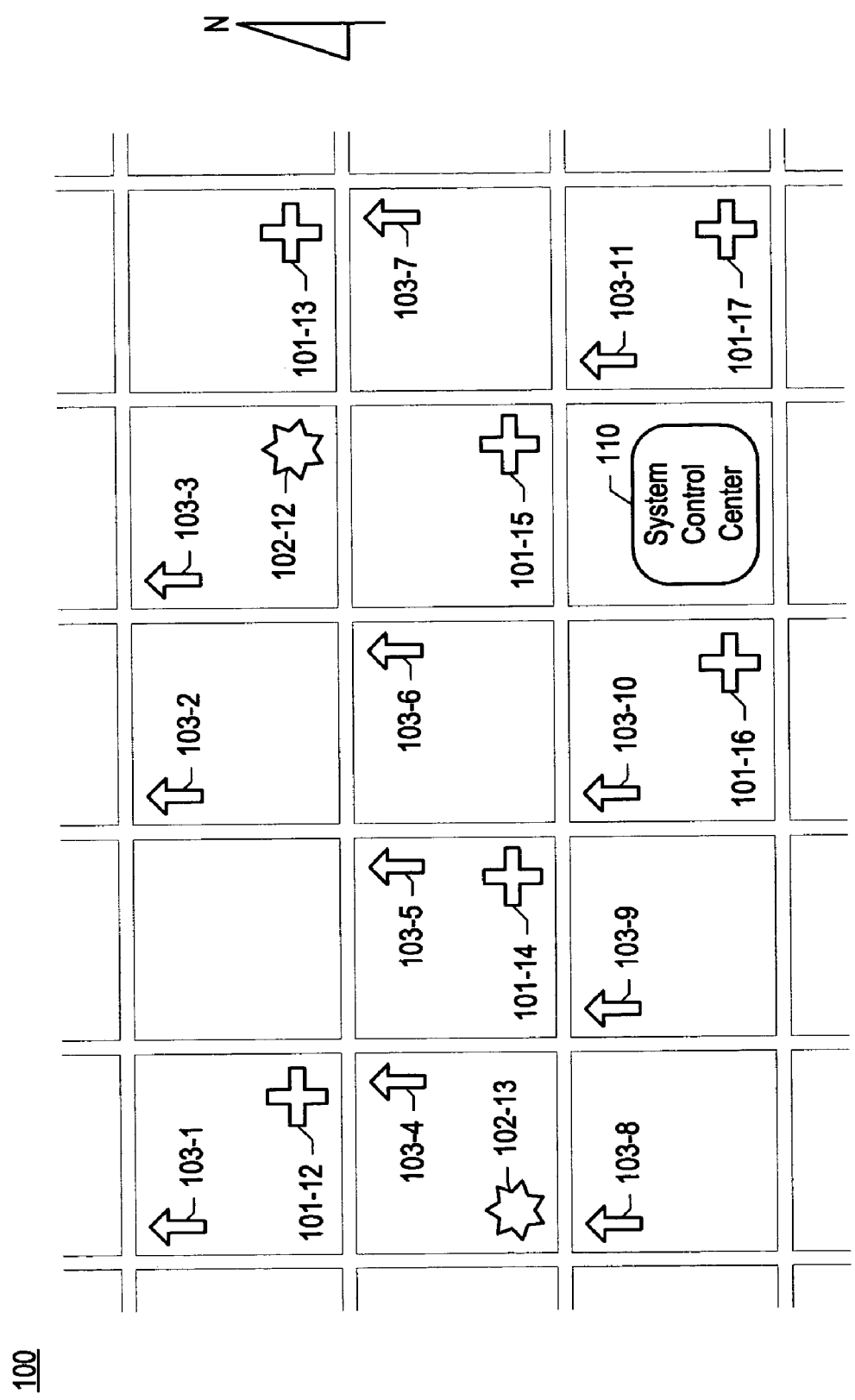
FIG. 1 depicts a city map and the location of the salient components of the illustrative embodiment of the present invention on that map.

FIG. 1 depicts a city map and the location of the salient components of the illustrative embodiment of the present invention on that map. The illustrative embodiment comprises:

i. seventeen (17) spatially-disparate environmental sensor arrays 101-1 through 101-17, ii. thirteen (13) spatially-disparate video camera clusters 102-1 through 102-13, iii. eleven (11) spatially-disparate hazardous material detection stations 103-1 through 103-11, and iv. system control center 110.

Environmental sensor arrays 101-1 through 101-11 and video camera clusters 102-1 through 102-11 are not distinctly shown in FIG. 1 because they are co-located with and contained within hazardous material detection stations 103-1 through 103-11, respectively.

Environmental sensor arrays 101-1 through 101-17, video camera clusters 102-1 through 102-13, and hazardous material detection stations 103-1 through 103-11 are deployed throughout city 100 to enable the comprehensive environmental, video, and hazardous material surveillance of city 100. In accordance with the illustrative embodiment, all of environmental sensor arrays 101-1 through 101-17, video camera clusters 102-1 through 102-13, and hazardous material detection stations 103-1 through 103-11 are outdoors, but after reading this specification it will be clear to those skilled in the art how to make and use embodiments of the present invention in which some or all of the environmental sensor arrays, video camera clusters, and hazardous material detection stations are indoors. Furthermore, although the illustrative embodiment is depicted as deployed in an urban environment, it will be clear to those skilled in the art, after reading this specification, how to make and use alternative embodiments of the present invention that are deployed or deployable in other environs (e.g., on ship board, in a rural area, in suburbia, etc.).

Each of environmental sensor arrays 101-1 through 101-17 monitors eight environmental characteristics (e.g., precipitation, humidity, sunlight, temperature, wind speed, wind direction, barometric pressure, ambient sound, etc.) at a different location and reports its findings to system control center 110. Furthermore, each of environmental sensor arrays 101-1 through 101-11 reports its findings to hazardous material detection stations 103-1 through 103-11, respectively. In accordance with the illustrative embodiment, the reporting is accomplished through wireline telemetry in well-known fashion. It will be clear to those skilled in the art, however, after reading this specification, how to make and use alternative embodiments of the present invention in which some or all of the reporting is accomplished through wireless telemetry. The details of environmental sensor arrays 101-1 through 101-17 are described below and with respect to FIG. 2.

Each of video camera clusters 102-1 through 102-13 monitors a location, in well-known fashion, and transmits its video signals to system control center 110 via wireline telemetry. It will be clear to those skilled in the art, however, how to make and use alternative embodiments of the present invention in which some or all of the video signals are transmitted via wireless telemetry. The details of video camera clusters 102-1 through 102-13 are described below and with respect to FIG. 3.

Each of hazardous material detection stations 103-1 through 103-11 measures the amount of six (6) hazardous materials (e.g., nuclear warfare agents, chemical warfare agents, biological warfare agents, etc.) and transmits an alarm status for each hazardous material to system control center 110 via wireline telemetry. It will be clear to those skilled in the art, however, how to make and use alternative embodiments of the present invention in which some or all of the alarms are transmitted via wireless telemetry. Although each of hazardous material detection stations 103-1 through 103-11 detects six (6) hazardous materials, it will be clear to those skilled in the art, after reading this specification, how to make and use embodiments of the present invention that detect any number of hazardous materials. The details of hazardous material detection stations 103-1 through 103-11 are described below and with respect to FIGS. 4 through 6.

Although the illustrative embodiment comprises 17 environmental sensor arrays, 13 video camera clusters, and 11 hazardous material detection stations, it will be clear to those skilled in the art, after reading this specification, how to make and use embodiments of the present invention that comprise any number of environmental sensor arrays, video camera clusters, and hazardous material detection stations. Furthermore, it will be clear to those skilled in the art, after reading this specification, how to make and use alternative embodiments of the present invention in which one or more of the hazardous material detection stations lacks a video camera cluster or an environmental sensor array or both.

System control center 110 receives the telemetry from environmental sensor arrays 101-1 through 101-17, video camera clusters 102-1 through 102-13, and hazardous material detection stations 103-1 through 103-11 and determines, in the manner described below, whether or not to issue a system-wide alarm. The operation of environmental sensor arrays 101-1 through 101-17, video camera clusters 102-1 through 102-13, hazardous material detection stations 103-1 through 103-11, and system control center 110 are described in detail below and with respect to FIGS. 8 through 11.

Figure 2:
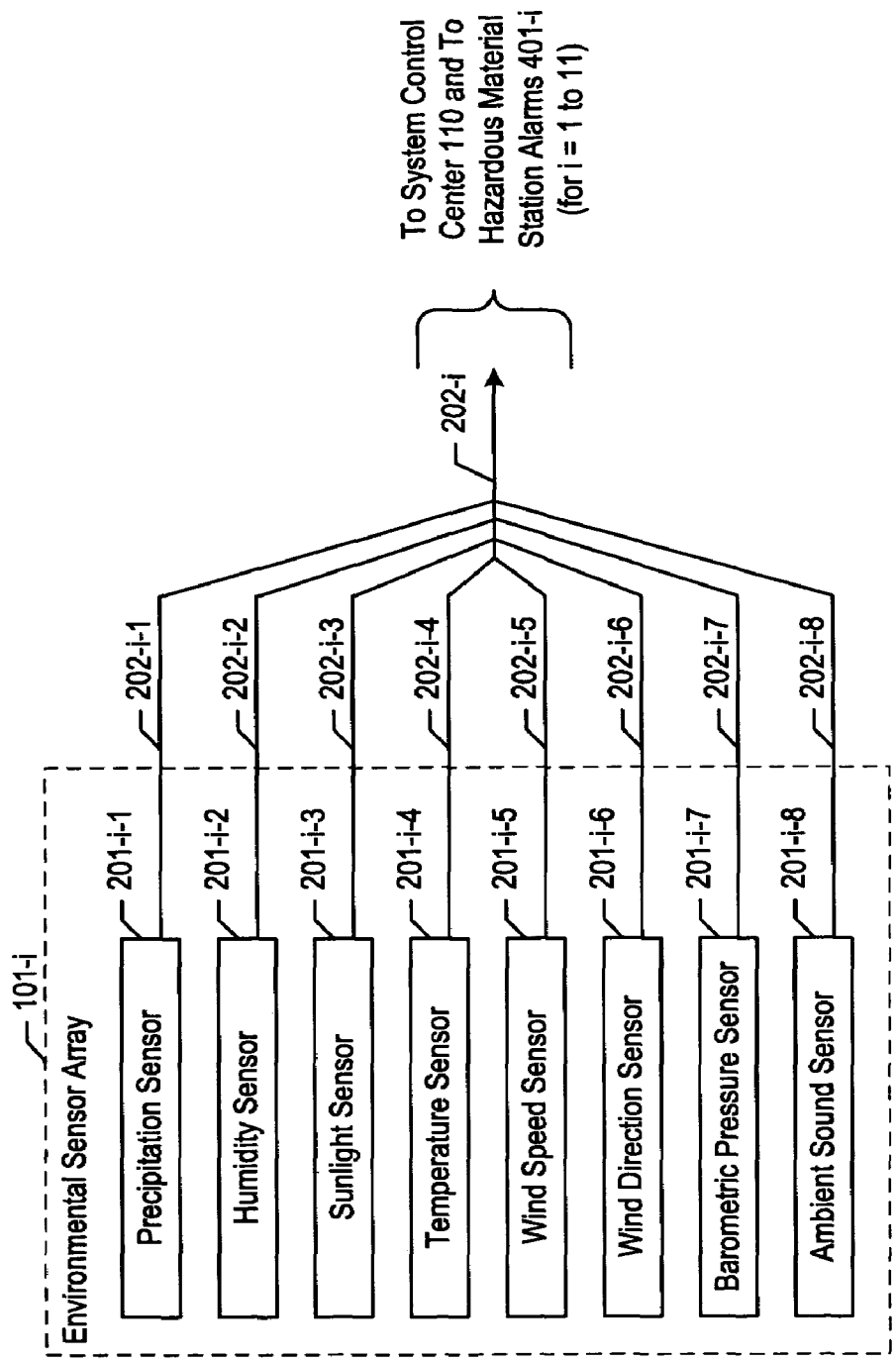
FIG. 2 depicts a block diagram of the salient components of each of environmental sensor arrays 101-1 through 101-17.

FIG. 2 depicts a block diagram of the salient components of each of environmental sensor arrays 101-1 through 101-17. Environmental sensor array 101-i, for i=1 through 17, comprises:

i. precipitation sensor 201-i-1,
ii. humidity sensor 201-i-2,
iii. sunlight sensor 201-i-3,
iv. temperature sensor 201-i-4,
v. wind speed sensor 201-i-5,
vi. wind direction sensor 201-i-6,
vii. barometric pressure sensor 201-i-7, and
viii. ambient sound sensor 201-i-8. The illustrative embodiment measures these eight environmental factors because each of them can—for the reasons described below—be correlated to the efficacy, and, therefore, the likelihood of a chemical, biological, radiological, or nuclear weapons attack.

In accordance with the illustrative embodiment, each of environmental sensor arrays 101-1 through 101-17 comprises the same eight sensors. It will be clear to those skilled in the art however, after reading this specification, how to make and use alternative embodiments of the present invention in which each sensor array has any subset of these sensors. Furthermore, it will be clear to those skilled in the art, after reading this specification, how to make and use alternative embodiments of the present invention that measure one or more additional environmental factors that can be correlated to the efficacy, and, therefore, the likelihood of a chemical, biological, radiological, or nuclear weapons attack.

The output of each sensor is multiplexed into environmental telemetry feed 202-i in well-known fashion and transmitted to system control center 110 and, for k=1 through 11 to hazardous material station alarms 402-k, respectively. It will be clear to those skilled in the art how to make each of environmental sensor arrays 101-1 through 101-17.

Figure 3:
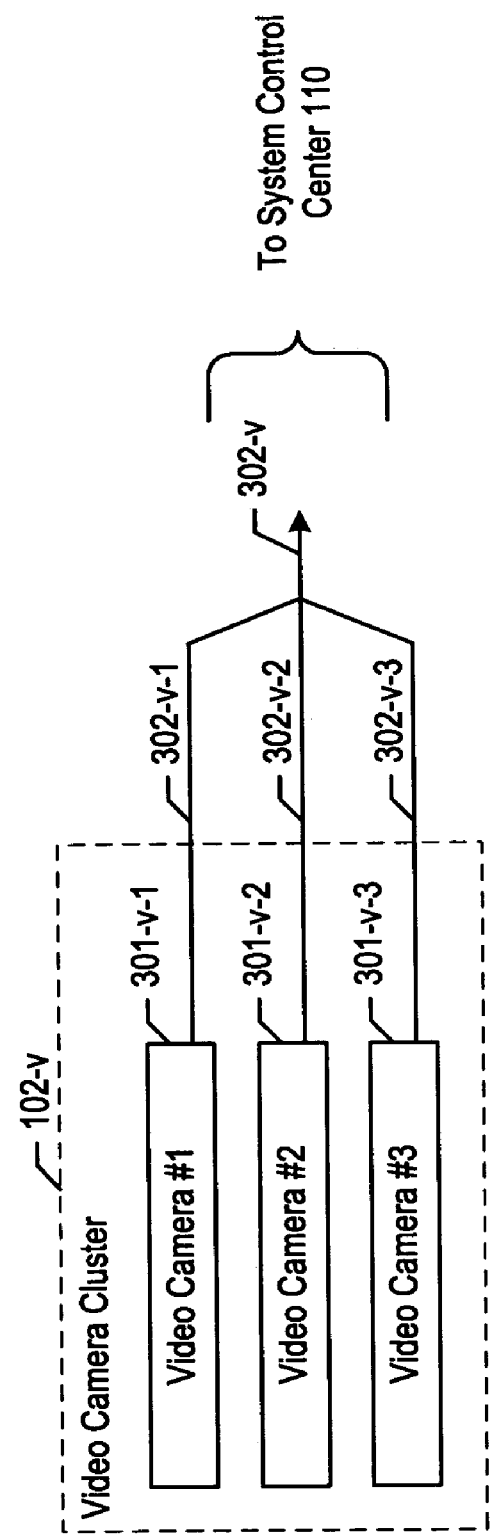
FIG. 3 depicts a block diagram of the salient components of each of video camera clusters 102-1 through 102-13.

FIG. 3 depicts a block diagram of the salient components of each of video camera clusters 102-1 through 102-13. Video camera cluster 102-v, for v=1 through 13, comprises: video camera #1, video camera #2, and video camera #3. The output of each camera is multiplexed in well-known fashion and transmitted to system control center 110 via wireline telemetry feed 302-v. It will be clear to those skilled in the art how to make each of video camera clusters 102-1 through 102-13.

In accordance with the illustrative embodiment, each of video camera clusters 102-1 through 102-13 comprises three cameras. It will be clear to those skilled in the art however, after reading this specification, how to make and use alternative embodiments of the present invention in which each video camera cluster has any number of video cameras (including only one (1) camera).

Figure 4:
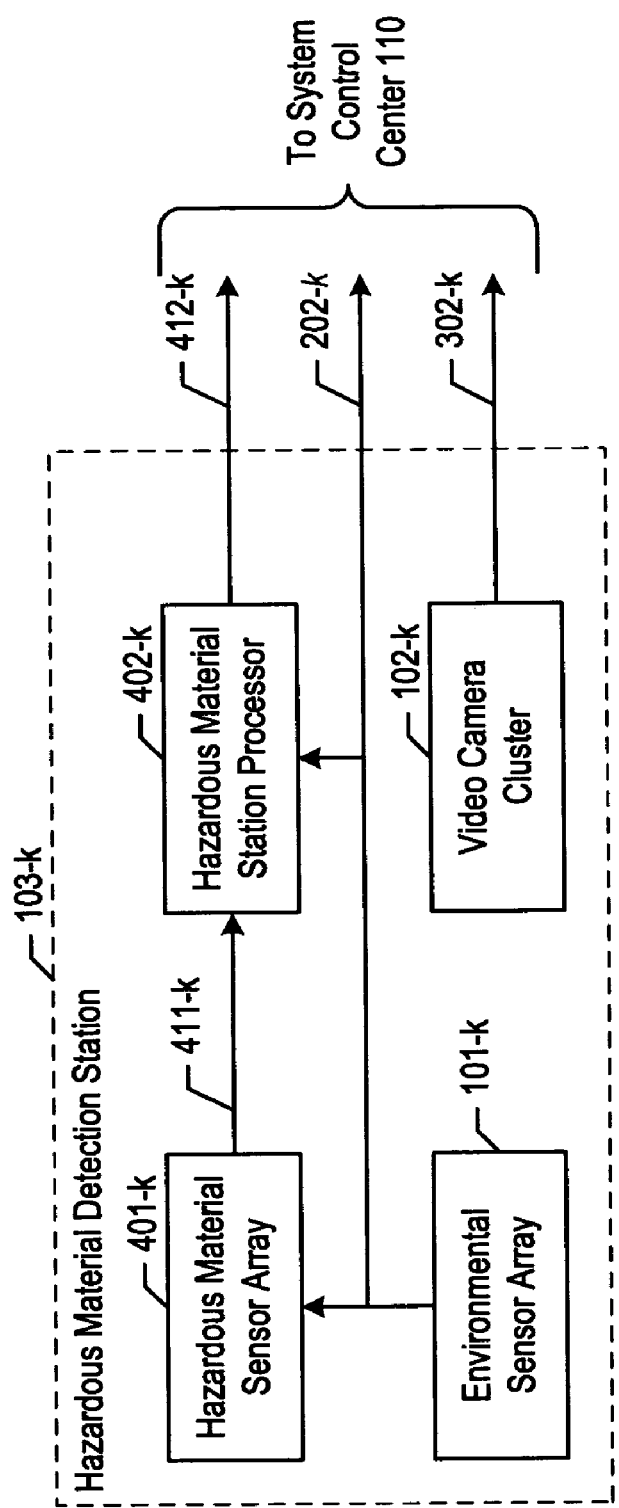
FIG. 4 depicts a block diagram of the salient components of each of hazardous material detection stations 103-1 through 103-11.

FIG. 4 depicts a block diagram of the salient components of each of hazardous material detection stations 103-1 through 103-11. Hazardous material detection station 103-k, for k=1 through K, comprises:

i. hazardous material sensor array 401-k,
    ii. hazardous material station processor 402-k,
    iii. environmental sensor array 101-k, and
    iv. video camera cluster 102-k, interconnected as shown.

Hazardous material sensor array 401-k comprises six hazardous material sensors for measuring the amount of alpha particles, beta particles, anthrax, small pox, sarin gas, and VX gas present at the array. In accordance with the illustrative embodiment of the present invention, hazardous material sensor array 401-k receives measurements on the current environmental factors from environmental sensor array 101-k and uses them to determine how frequently—and with what sensitivity—it should sample the ambient environment for the hazardous materials. This is because a chemical, biological, radiological, or nuclear attack is more likely to occur when some environmental factors are present than at other times, and, therefore, the illustrative embodiment is more diligent in looking for an attack when the environmental factors are more favorable for an attack.

Hazardous material sensor array 401-k does not determine whether the amount of a measured hazardous material should trip an alarm; this is performed by hazardous material station processor 402-k. To this end, the measurements made by hazardous material sensor array 401-k are transmitted to hazardous material station processor 402-k via wireline feed 411-k. The details of hazardous material sensor array 401-k are described below and with respect to FIG. 5.

Hazardous material station processor 402-k takes the measurements from hazardous material sensor array 401-k and the measurements from environmental sensor array 101-k and determines whether or not to transmit a "station" alarm to system control center 110 via wireline telemetry feed 412-k. In accordance with the illustrative embodiment, an alarm is not issued when the measured amount of a hazardous material reaches a static threshold. Instead, an alarm is issued when the amount of a hazardous material reaches a dynamic threshold, wherein the threshold changes and is based on at least one environmental factor. The purpose of having the threshold change as a function of one or more environmental factors is to recognize that a chemical, biological, radiological, or nuclear attack is more likely to occur when some environmental factors are present than at other times, and, therefore, the threshold for issuing an alarm should lower when the environmental factors are more favorable for an attack than when the factors are unfavorable for an attack. The threshold for each hazardous material can be changed independently of the threshold for the other hazardous materials, and the threshold for each threshold can be determined using a different function of the environmental factors. The details of hazardous material station processor 402-k are described in detail below and with respect to FIG. 6.

Hazardous material station processor 402-k comprises a general-purpose digital processor that performs an adaptive algorithm that sets the dynamic threshold based on measurements from environmental sensor array 101-k. In some alternative embodiments of the present invention, hazardous material station processor 402-k is a neural network.

Figure 5:
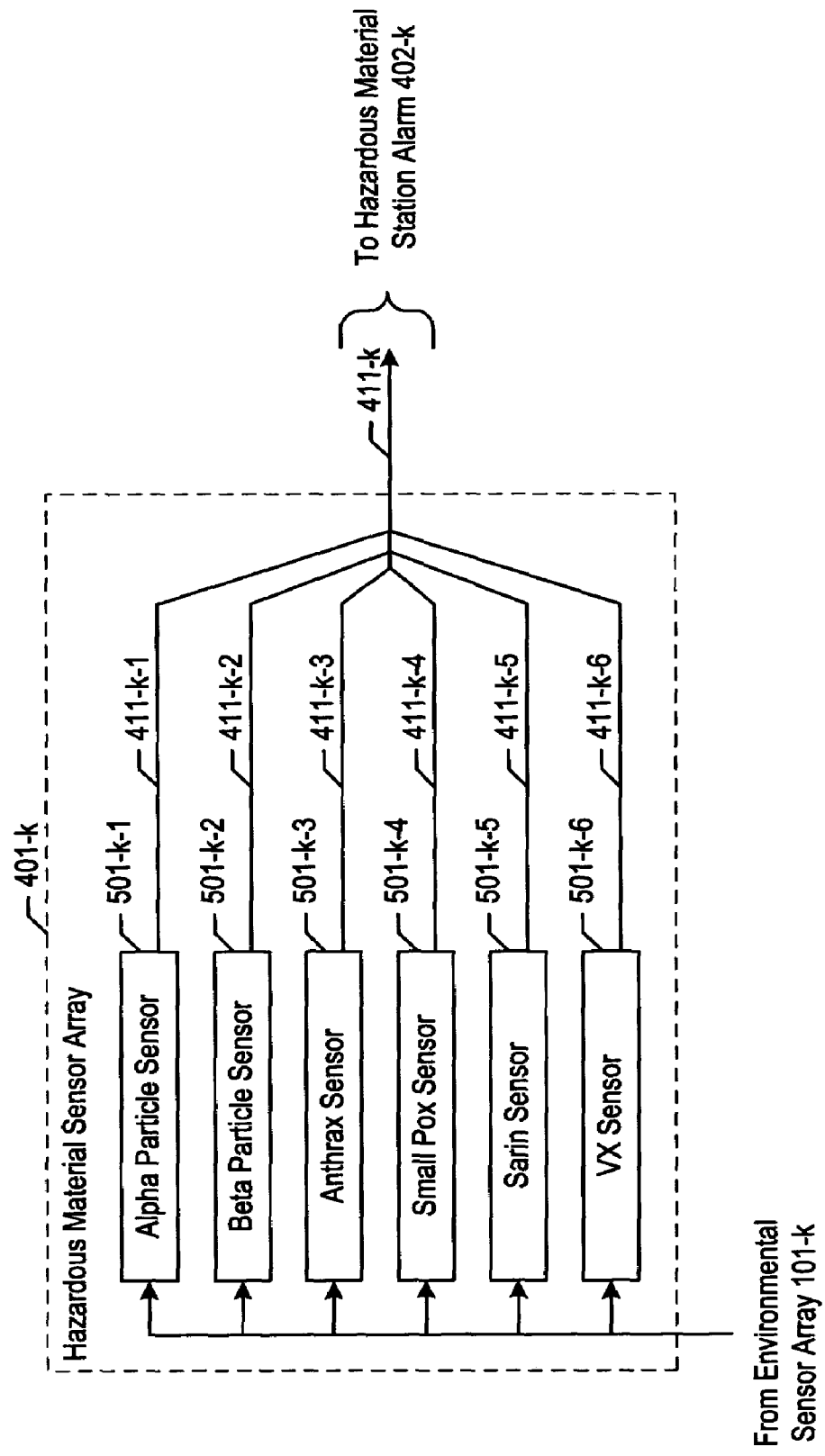
FIG. 5 depicts a block diagram of the salient components of hazardous material sensor array 401-k.

FIG. 5 depicts a block diagram of the salient components of hazardous material sensor array 401-k, which comprises:

i. alpha particle sensor 501-$k$-1,
    ii. beta particle sensor 501-k-2,
    iii. anthrax sensor 501-k-3,
    iv. small pox sensor 501-k-4,
    v. sarin gas sensor 501-k-5, and
    vi. VX gas sensor 501-k-6, interconnected as shown. Each of the six sensors is a point sensor and receives one or more measurements of the current ambient environment factors as observed by environmental sensor array 101-k and uses them to change the schedule or when—and with what care—it should sample the ambient environment for its specific hazardous material. In some alternative embodiments of the present invention, one or more of the sensors are stand-off sensors, in contrast to point sensors, and it will be clear to those skilled in the art, after reading this specification, how to make and use embodiments of the present invention which comprise point sensors, stand-off sensors, or a combination of point sensors and stand-off sensors.

In general, a chemical, biological, radiological, or nuclear attack is more likely to occur:

i. when it is not precipitating (e.g., raining, snowing, sleeting, etc.) because the precipitation frustrates the dissemination and enervates the efficacy of the hazardous materials;
    ii. when it is lower humidity, for the same reasons;
    iii. when it is night (i.e., there is no sunlight) because the sunlight tends to breakdown the biological and chemical agents, because attacks are more psychologically terrifying at night, and because inversion layers typically occur at night;
    iv. when the temperature is not extreme;
    v. when the wind is blowing because the wind helps to the disseminate the hazardous materials;
    vi. when the wind is blowing in a constant direction because it also helps to disseminate the hazardous materials;
    vii. when a rising barometric pressure suggests that fair weather is coming; and
    viii. shortly after a sound that could be caused by a chemical explosion.

Therefore, the schedule for checking for each hazardous material should be faster or more frequent when the conditions are ripe for an attack with that type of material. The rate for checking for each hazardous material can be different than the rate for the other hazardous materials, and the rate for checking for each hazardous material can be a different function of environmental factors. After reading this specification, it will be clear to those skilled in the art how to make and use alpha particle sensor 501-k-1, beta particle sensor 501-k-2, anthrax sensor 501-k-3, pox sensor 501-k-4, sarin gas sensor 501-k-5, and VX gas sensor 501-k-6.

Figure 6:
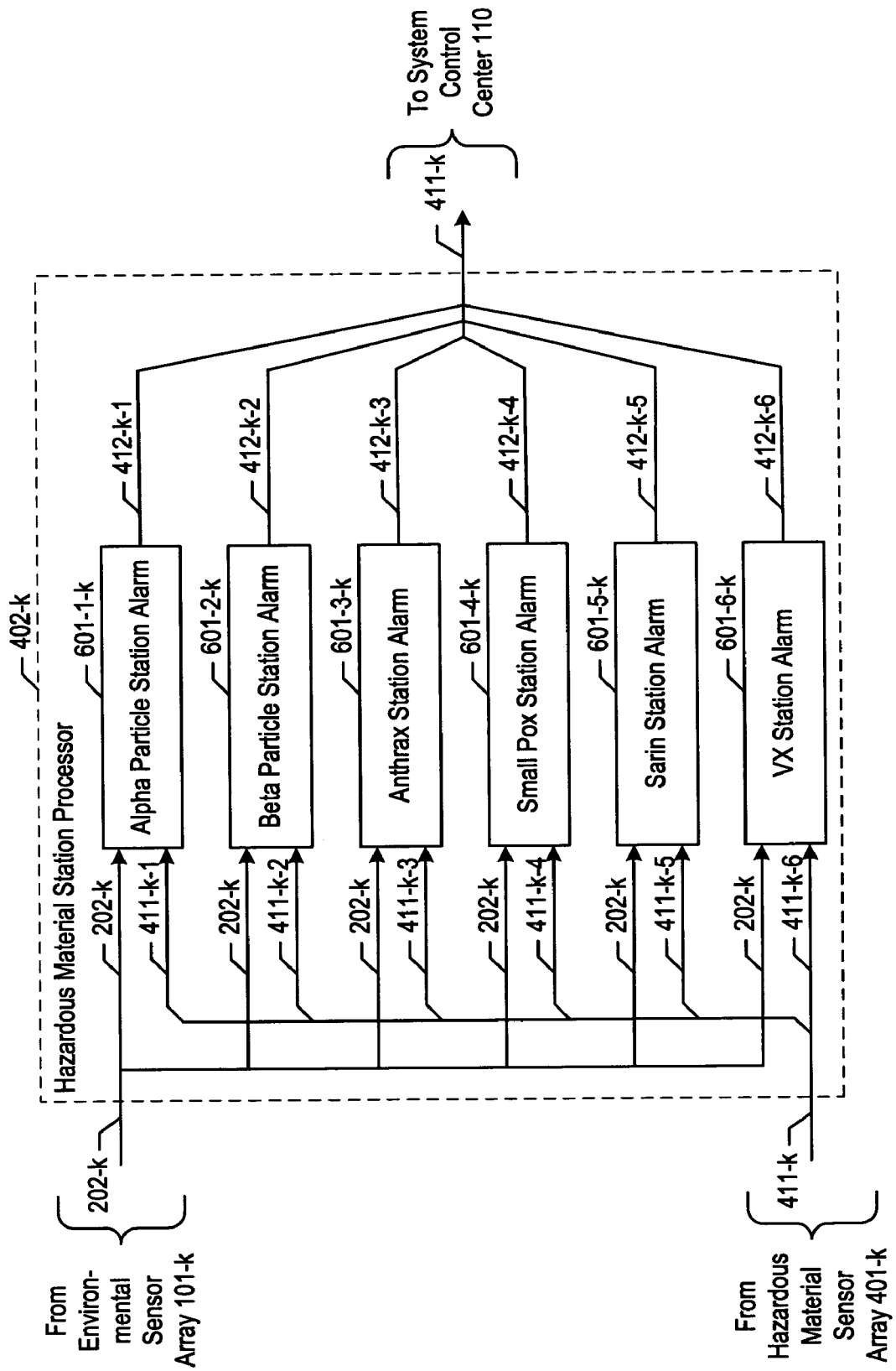
FIG. 6 depicts a block diagram of the salient components of hazardous material station processor 402-k.

FIG. 6 depicts a block diagram of the salient components of hazardous material station processor 402-k, which comprises:

i. alpha particle station alarm 601-k-1,
    ii. beta particle station alarm 601-k-2, iii. anthrax station alarm 601-k-3,
iv. small pox station alarm 601-k-4,
v. sarin gas station alarm 601-k-5, and
vi. VX gas station alarm 601-k-6, interconnected as shown.

Each of these six station alarms receives:
i. one or more measurements of the current ambient environment factors as observed by environmental sensor array 101-k, and
ii. a stream of measurements from its corresponding sensor in hazardous material sensor array 401-k, and uses them to determine when an alarm for that hazardous material should be transmitted to system control center 110 via wireline 411-k. Each of the six station alarms is issued when the amount of a hazardous material reaches a threshold, and an alarm is stopped when the amount of the hazardous material falls below the threshold. A station can issue one or more alarms concurrently.

The thresholds are not static, however, but change and are at least partially based on one or more of the measurements of the current ambient environment factors as observed by environmental sensor array 101-k. In particular, a chemical, biological, radiological, or nuclear attack is more likely to occur when some environmental conditions are present, and, therefore, the individual thresholds for each alarm are higher when those environmental conditions do not exist. For example, the threshold for sarin is higher when it is precipitating than when it is not precipitating, lower when it is lower humidity than higher humidity, lower when it is night than when it is day, and lower when it is windy than when it is not windy. The operation of hazardous material station processor 402-k is described in detail below and with respect to FIGS. 8 through 11.

Figure 7:
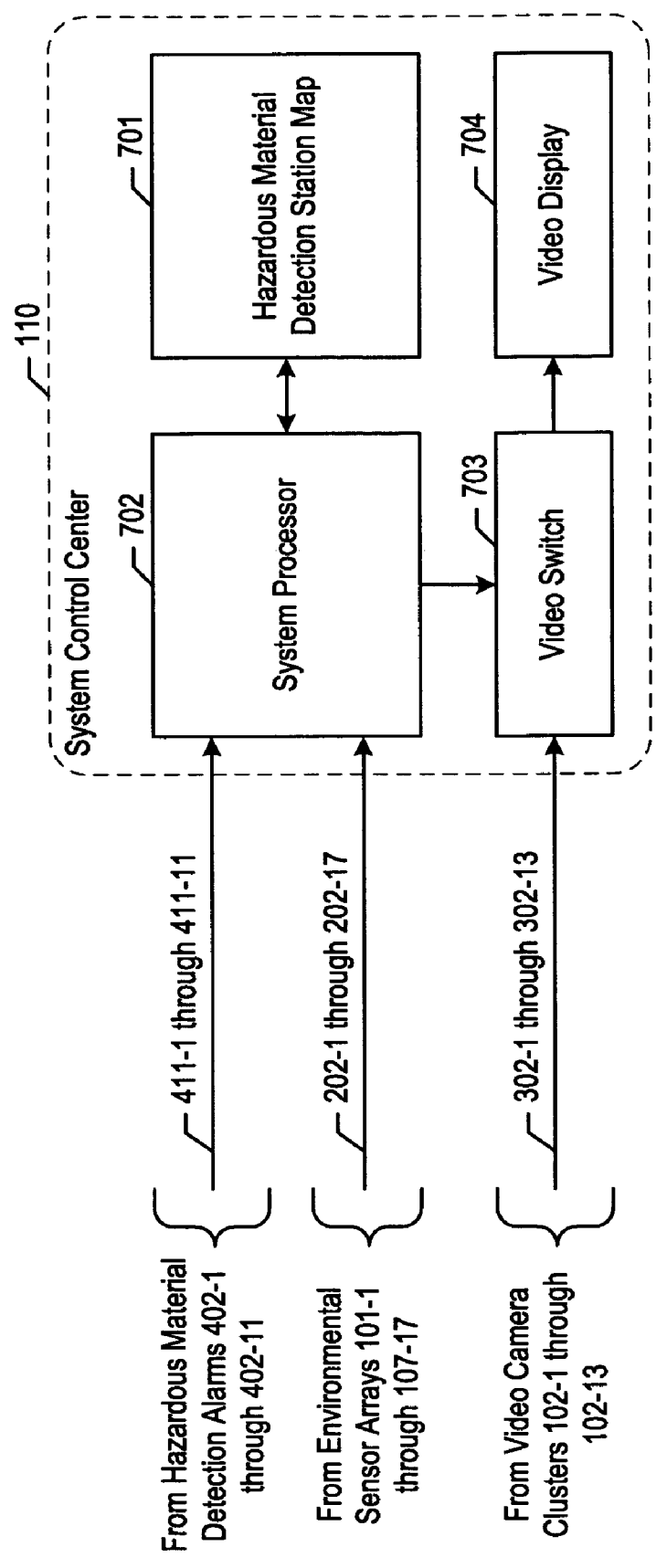
FIG. 7 depicts a block diagram of the salient components of system control center 110.

FIG. 7 depicts a block diagram of the salient components of system control center 110, which comprises:
i. hazardous material detection station map 701,
ii. system processor 702,
iii. video switch 703, and
iv. video display 704, interconnected as shown.

One of the advantages of the illustrative embodiment is that it incorporates mechanisms that seek to thwart false system alarms. One of these mechanisms is based on the understanding that a chemical, biological, radiological, or nuclear weapon attack is more likely to issue when there are alarms from multiple stations that are near each other than when there are alarms from multiple stations that are not near each other (e.g., are randomly distributed around the area that is monitored, etc.). To facilitate this analysis, the illustrative embodiment comprises a map—hazardous material detection station map 701—that associates each hazardous material detection station to its location (e.g., latitude and longitude, etc.).

Another of the mechanisms that the illustrative embodiments uses to prevent false system alarms is based on the understanding that alarms from multiple stations are more likely to occur temporally in the same direction as the wind—as the hazardous material is blown downwind and into contact with the various hazardous material detection stations. To facilitate this analysis, hazardous material detection station map 701 also associates each environmental sensor array to its location.

In accordance with the illustrative embodiment, hazardous material detection station map 701 is a data structure, such as that depicted in Table 1.

TABLE 1

Hazardous Material Detection Station Map 701

| | Latitude | Longitude |
|---|---|---|
| Hazardous Material Detection Station 411-1 | 40° 35' 56.03" N. | 140° 35' 46.44" E. |
| Hazardous Material Detection Station 411-2 | 40° 34' 26.83" N. | 140° 36' 36.02" E. |
| ... | ... | ... |
| Hazardous Material Detection Station 411-11 | 40° 36' 36.14" N. | 140° 38' 56.33" E. |
| Environmental Sensor Array 101-12 | 40° 35' 56.66" N. | 140° 33' 14.03" E. |
| Environmental Sensor Array 101-13 | 40° 36' 49.35" N. | 140° 35' 06.55" E. |
| ... | ... | ... |
| Environmental Sensor Array 101-17 | 40° 37' 35.93" N. | 140° 35' 52.83" E. |

It will be clear to those skilled in the art how to make hazardous material detection station map 701.

System processor 702 receives the telemetry from hazardous material detection alarms 411-1 through 411-11, the telemetry from environmental sensor arrays 101-1 through 101-17, and the location data from hazardous material detection station map 701 and determines whether or not to issue a system alarm. In accordance with the illustrative embodiment, system processor 702 is a general-purpose processor that is programmed to perform the functionality described herein and with respect to FIGS. 8 through 11.

When system processor 702 determines that an attack has occurred or is occurring, it issues a system alarm to the personnel who monitor the illustrative embodiment (who are not shown in FIG. 7) and it directs video switch 703 to automatically route the video feed(s) for the area(s) where the attack has occurred or is occurring to video display 704. This enables the personnel who monitor the illustrative embodiment to further verify the attack. For example, if system processor 702 determines that a chemical gas attack is occurring in Times Square, then video of people collapsing and convulsing in Times Square will enable the personnel who monitor the illustrative embodiment to verify that indeed a gas attack has occurred. In contrast, if system processor 702 determines that a chemical gas attack is occurring in Times Square, then video showing people going about their business as usual will suggest to the personnel who monitor the illustrative embodiment that it is a false alarm or that it should be investigated more thoroughly.

Video switch 703 is controllable by system processor 702 as it is well known to those skilled in the art, and video display 704 is also well known to those skilled in the art.

Figure 8:
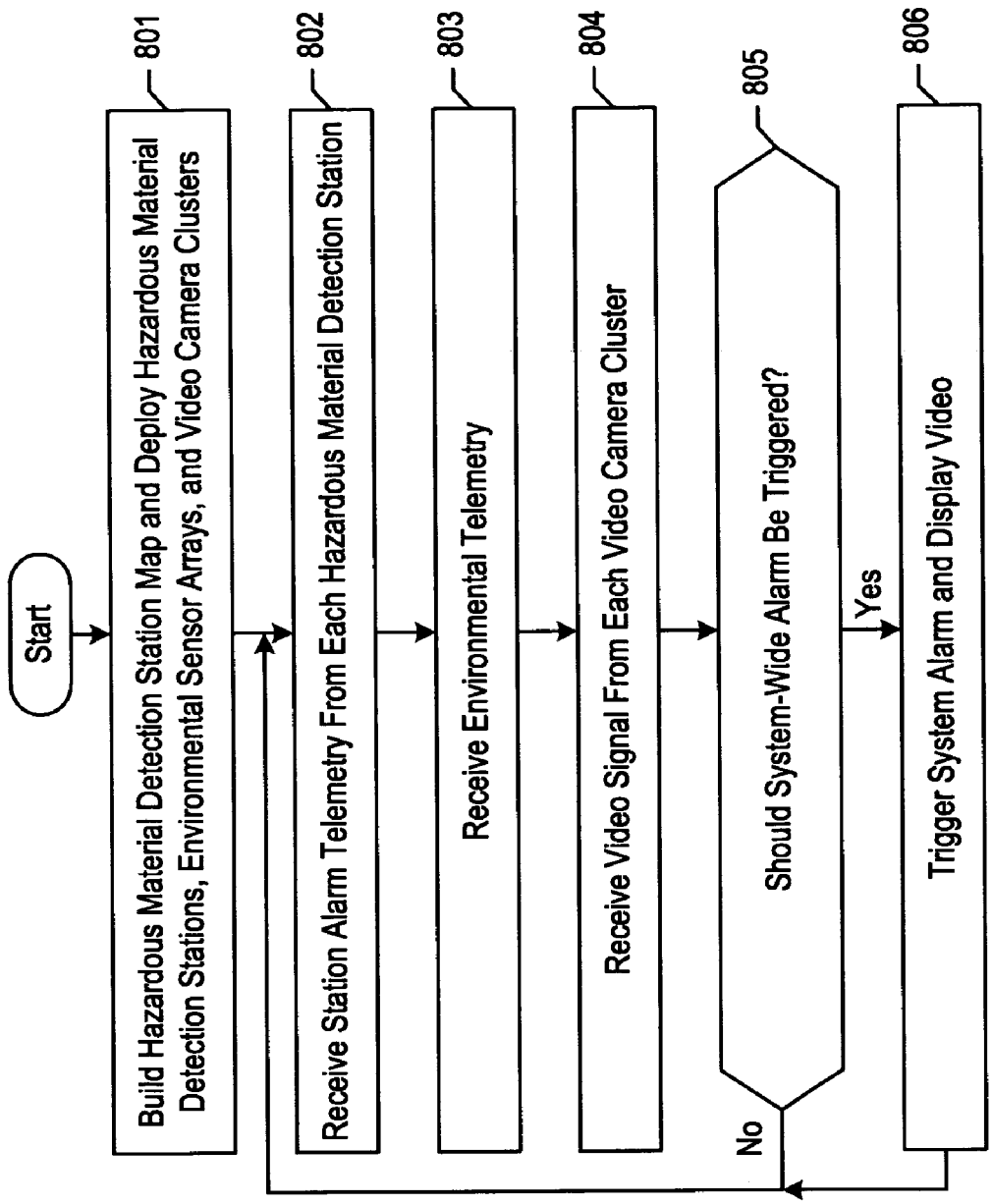
FIG. 8 depicts a flowchart of the salient tasks associated with the deployment and operation of the illustrative embodiment.

FIG. 8 depicts a flowchart of the salient tasks associated with the deployment and operation of the illustrative embodiment.

At task 801, hazardous material detection station map 701 is built and environmental sensor arrays 101-1 through 101-17, video camera clusters 102-1 through 102-13, and hazardous material detection stations 103-1 through 103-11 are deployed throughout city 100 in accordance with hazardous material detection station map 701. It will be clear to those skilled in the art, after reading this specification, how to perform task 801.

At task 802, system processor 702 in system control center 110 continually receives the station alarm status from each of the six station alarms for each of the eleven hazardous material detection stations (i.e., system processor 702 periodically receives the station alarm status for all 11×6=66 station alarms). In the best of cases, system processor 702 does not receive any station alarms.

At task 803, system processor 702 in system control center 110 continually receives the environmental telemetry transmitted from each of the eight environmental sensors for each of the sixteen environmental sensor arrays (i.e., system processor 702 periodically receives the environmental data for all 16×8=128 environmental sensors).

At task 804 system processor 702 in system control center 110 continually receives the video signals from each of the thirteen video surveillance clusters. In accordance with the illustrative embodiment, tasks 802, 803, and 804 are performed concurrently, but it will be clear to those skilled in the art, after reading this specification, how to make and use alternative embodiments of the present invention in which tasks 802, 803, and 804 are performed in any order.

At task 805, system processor 702 in system control center 110 determines whether a system-wide alarm should be issued. In accordance with the illustrative embodiment, system processor 702 determines whether to issue a system-wide alarm based on:

i. the number of station alarms that are received,
 ii. the number of hazardous materials that are detected,
 ii. the proximity of the station alarms, when there is more than one station alarm,
 iv. the temporal sequence in which the station alarms are received, when there is more than one station alarm, and
 v. the environmental conditions (including wind direction).

It will be clear to those skilled in the art, however, after reading this specification, how to make and use alternative embodiments of the present invention that omit one or more of these factors. When system processor 702 determines that an alarm should be issued, control passes to task 806; otherwise control returns to task 802. The details of task 805 are described below and with respect to FIG. 9.

At task 806, system processor 702 issues a system-wide alarm and directs video switch 703 to direct the video telemetry from areas where the station alarms are coming to video display 704. After task 806 has been performed, control returns to task 802.

Figure 9:
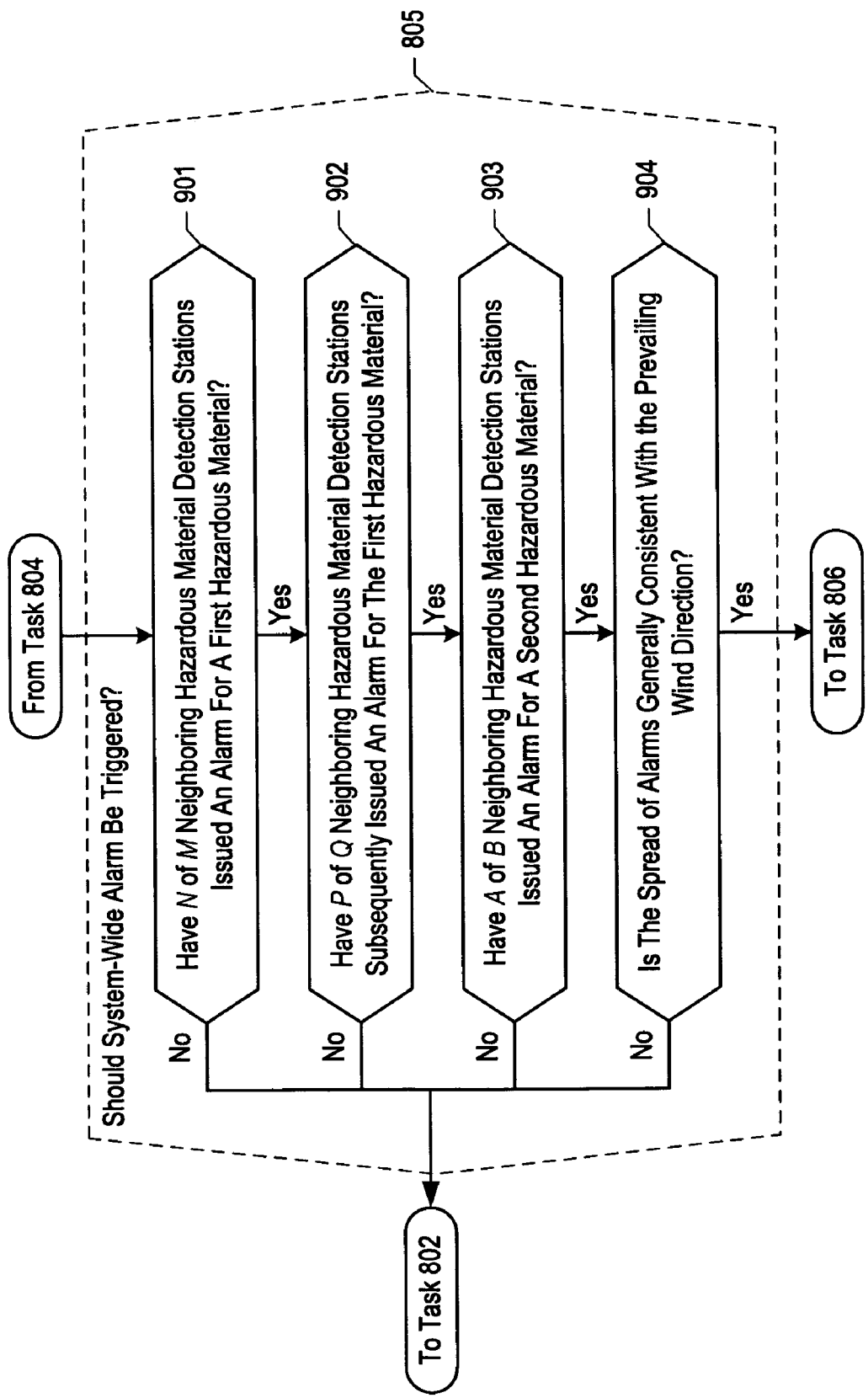
FIG. 9 depicts a flowchart of the salient tests in task 805 of FIG. 8.

FIG. 9 depicts a flowchart of the salient tests in task 805 of FIG. 8. It will be clear to those skilled in the art, after reading this specification, how to make and use embodiments of the present invention that omit one or more of the tests.

At test 901, system processor 702 determines whether at least N of M neighboring hazardous material detection stations issued an alarm for a first hazardous material, wherein N and M are positive integers, wherein 2≦N≦M≦K, and wherein at least one of N and M change based on an environmental factor. Test 901 incorporates three different mechanisms for reducing the probability that a false system-wide alarm will be issued.

The first mechanism requires that at least N (wherein 2≦N) stations report an alarm for the same hazardous material within an interval of time. This prevents a false alarm from one hazardous material detection station from issuing a false system-wide alarm. If the probability of a station issuing a false alarm is p and the probability of each station issuing a false alarm is independent of another station issuing a false alarm, then the probability that the illustrative embodiment will issue a false system-wide alarm is no higher than $p^N$. The implication is that the probability of issuing a false system-wide alarm is affected by the value of N. High values of N lower the likelihood of a false system-wide alarm, but also increase the likelihood that a real system-wide alarm will not issue. It will be clear to those skilled in the art, after reading this specification, how to select values for N based on the acceptable likelihood of a false system-wide alarm and on the likelihood that a real system-wide alarm will not issue.

The second mechanism requires that the N stations reporting an alarm for the same hazardous material within an interval of time be a subset of M neighboring stations (i.e., have some proximity to each other). For the purpose of this specification, M stations are "neighboring stations" if and only if a circle exists that contains all M stations and no other stations. System processor 702 uses Hazardous Material Detection Station Map 701 to determine if a circle exists that contains all M stations and no other stations.

The purpose of this mechanism is to issue a system-wide alarm only when the N stations reporting an alarm for the same hazardous material within an interval of time have some proximity to each other. This is based on the assumption that a real attack is more likely to be detected by stations that are near each other than by stations that have no proximity. Small values of M lower the likelihood of a false system-wide alarm, but also increase the likelihood that a real system-wide alarm will not issue. It will be clear to those skilled in the art, after reading this specification, how to select values for M based on the acceptable likelihood of a false system-wide alarm and on the likelihood that a real system-wide alarm will not issue.

The third mechanism changes the values of at least one of N and M based on at least one environmental factor (e.g., precipitation, wind speed, the amount of sunlight, etc.) to cause the threshold for a system-wide alarm to be higher when the environmental factor(s) suggest that an attack is less likely. For example, the ratio of N:M will be higher when it is precipitating, when it is not windy, and when it is sunny. It will be clear to those skilled in the art, after reading this specification, how to change the values of N and M based on environmental factors based on the acceptable likelihood of a false system-wide alarm and on the likelihood that a real system-wide alarm will not issue.

In some alternative embodiments of the present invention, test 901 determines whether R% of the hazardous material detection stations within S meters issued an alarm for a first hazardous material, wherein R and S are positive real numbers, wherein 0%≦R%≦100% and wherein at least one of R and S change based on an environmental factor.

At test 902, system processor 702 determines whether at least P of Q neighboring hazardous material detection stations issued an alarm for the first hazardous material, wherein P and Q are positive integers, 2≦P≦Q≦K, N≦P and wherein at least one of P and Q change based on an environmental factor. The purpose of test 902 is to ensure that a system-wide alarm is only issued when the extent of the stations reporting an alarm expands, as would be expected in a real attack.

Test 902 incorporates three different mechanisms for reducing the likelihood that a false system-wide alarm will be issued, and these three mechanisms are analogous to those in test 901. Therefore, it will be clear to those skilled in the art, after reading this specification, how to select values for P and Q and how to change them based on environmental factors based on the acceptable likelihood of a false system-wide alarm and on the likelihood that a real system-wide alarm will not issue.

At test 903, system processor 702 determines whether at least A of B neighboring hazardous material detection stations issued an alarm for a second hazardous material, wherein A and B are positive integers, wherein $2 \leq A \leq B \leq K$, and wherein at least one of A and B change based on an environmental factor. The purpose of test 903 is to ensure that a system-wide alarm is only issued when a second hazardous material is detected in addition to the first hazardous material, as would be expected in some types of real attacks. For example, in a nuclear attack, the detection of alpha particles might be accompanied by the detection of beta particles. There are, of course, other kinds of attacks that involve only one type of hazardous material.

At test 903, system processor 702 determines whether at least R of S neighboring hazardous material detection stations issued an alarm for a second hazardous material, wherein R and S are positive integers, wherein $2 \leq R \leq S \leq K$, and wherein at least one of R and S change based on an environmental factor. The purpose of test 903 is to ensure that a system-wide alarm is only issued when a second hazardous material is detected in addition to the first hazardous material, as would be expected in some types of real attacks. For example, in a nuclear attack, the detection of alpha particles might be accompanied by the detection of beta particles. There are, of course, other kinds of attacks that involve only one type of hazardous material.

In some alternative embodiments of the present invention, test 903 determines whether E% of the hazardous material detection stations within F meters issued an alarm for a second hazardous material, wherein E is a positive real number, wherein $0\% \leq E\% \leq 100\%$, and wherein at least one of E and F change based on an environmental factor.

Test 903 incorporates three different mechanisms for reducing the likelihood that a false system-wide alarm will be issued, and these three mechanisms are analogous to those in test 901. Therefore, it will be clear to those skilled in the art, after reading this specification, how to select values for A and B and how to change them based on environmental factors based on the acceptable likelihood of a false system-wide alarm based and on the likelihood that a real system-wide alarm will not issue.

At test 904, system processor 702 determines whether the spread of station alarms is generally consistent with the prevailing wind direction, as would be expected in a real attack as the hazardous material is blown downwind. To do this processor 702 uses its knowledge of the position of the stations reporting alarms, hazardous material detection station map 701, and its knowledge of the prevailing wind direction, which it gleans from the environmental sensor arrays in the vicinity of the stations reporting alarms. It will be clear to those skilled in the art, after reading this specification, how to make and use embodiments of the present invention that decide whether the spread of station alarms is generally consistent with the prevailing wind direction.

Figure 10:
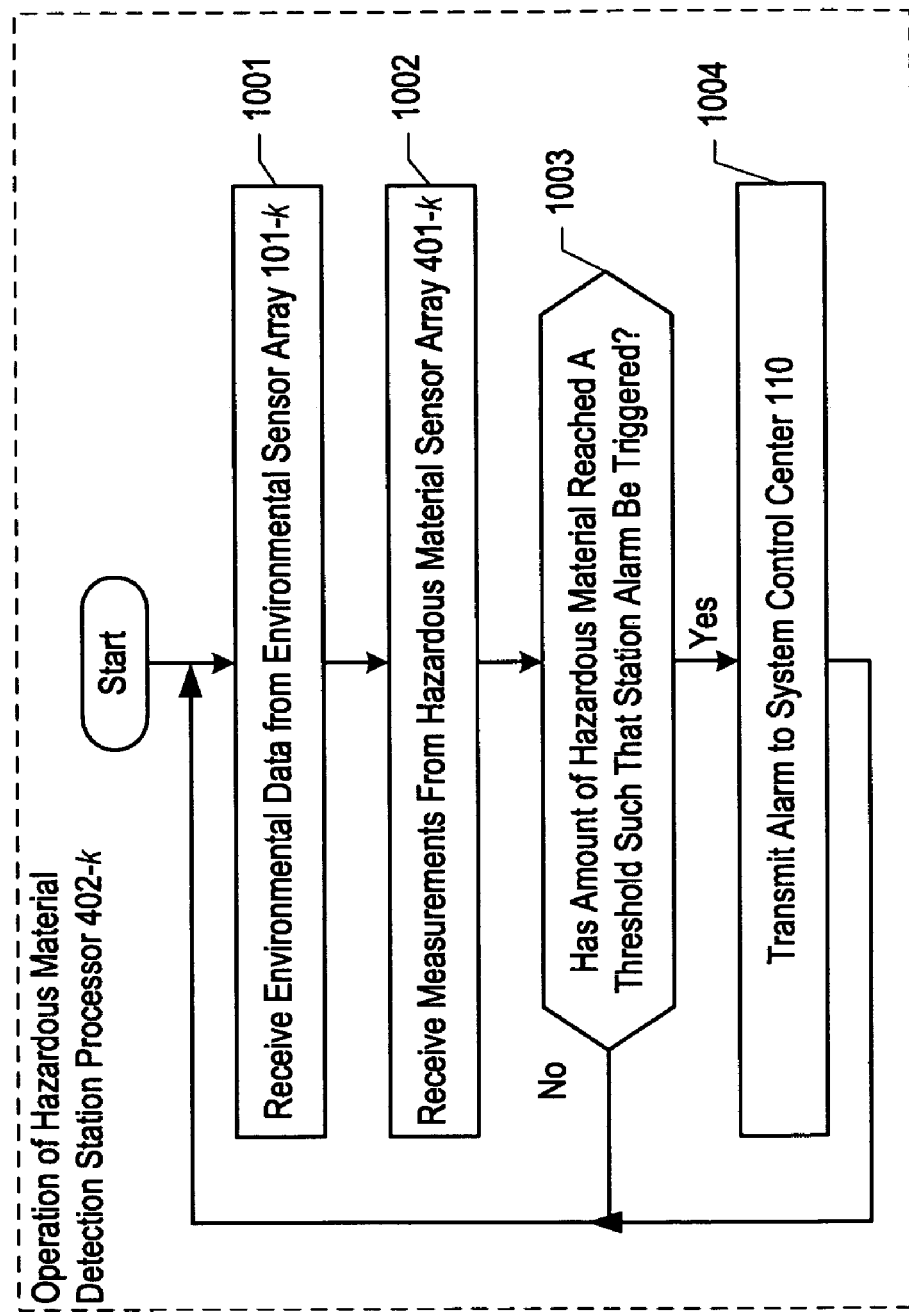
FIG. 10 depicts a flowchart of the salient tasks associated with the operation of hazardous material detection processor 402-k.

FIG. 10 depicts a flowchart of the salient tasks associated with the operation of hazardous material detection processor 402-k.

At task 1001, hazardous material detection processor 402-k receives the environmental data from environmental sensor array 101-k. It will be clear to those skilled in the art how to make and use embodiments of the present invention that perform task 1001.

At task 1002, hazardous material detection processor 402-k receives the hazardous material measurements from hazardous material sensor array 401-k. It will be clear to those skilled in the art how to make and use embodiments of the present invention that perform task 1002. Furthermore, it will be clear to those skilled in the art, after reading this specification, how to make and use embodiments of the present invention that perform tasks 1001 and 1002, concurrently or in any order.

At task 1003, hazardous material detection processor 402-k determines, based on the measurements received in task 1002 and the environmental data received in task 1001, whether the amount of a hazardous material has reached a threshold such that the station's alarm should be issued. When hazardous material detection processor 402-k determines that the alarm should be issued, control passes to task 1004; otherwise control returns to task 1001.

Hazardous material detection processor 402-k incorporates a mechanism to reduce the probability that a false station alarm will be issued. In particular, hazardous material detection processor 402-k changes the threshold for each hazardous material based, at least in part, on the environmental data received in task 1001. For example, FIG. 11 depicts the threshold for VX Gas in parts per million (ppm) as a function of both precipitation and whether or not it is sunny. From FIG. 11, it can be seen that the threshold is higher when it is precipitating and sunny than when it is not precipitation or not sunny or neither precipitating nor sunny.

At task 1004, hazardous material detection processor 402-k transmits a station alarm to system control center 110, via wireline 412-k. After task 1004, control returns to task 1001 to determine if an alarm for a second hazardous material should be issued and to determine if the amount of the first hazardous material has fallen (or the threshold raised) such that the alarm should be discontinued.

It is to be understood that the above-described embodiments are merely illustrative of the present invention and that many variations of the above-described embodiments can be devised by those skilled in the art without departing from the scope of the invention. For example, in this Specification, numerous specific details are provided in order provide a thorough description and understanding of the illustrative embodiments of the present invention. Those skilled in the art will recognize, however, that the invention can be practiced without one or more of those details, or with other methods, materials, components, etc.

Furthermore, in some instances, well-known structures, materials, or operations are not shown or described in detail to avoid obscuring aspects of the illustrative embodiments. It is understood that the various embodiments shown in the Figures are illustrative, and are not necessarily drawn to scale. Reference throughout the specification to "one embodiment" or "an embodiment" or "some embodiments" means that a particular feature, structure, material, or characteristic described in connection with the embodiment(s) is included in at least one embodiment of the present invention, but not necessarily all embodiments. Consequently, the appearances of the phrase "in one embodiment," "in an embodiment," or "in some embodiments" in various places throughout the Specification are not necessarily all referring to the same embodiment. Furthermore, the particular features, structures, materials, or characteristics can be combined in any suitable manner in one or more embodiments. It is therefore intended that such variations be included within the scope of the following claims and their equivalents.

What is claimed is:

1. A system comprising:
   a first environmental sensor for monitoring a first environmental characteristic;
   a first hazardous material sensor for measuring the amount of a first hazardous material; and a first alarm that is issued when the amount of said first hazardous material reaches a first threshold, wherein said first threshold changes and is based on said first environmental characteristic.

2. The system of claim 1 wherein said first environmental characteristic is precipitation.

3. The system of claim 2 wherein said first threshold is higher when it is precipitating than when it is not precipitating.

4. The system of claim 1 wherein said first environmental characteristic is humidity.

5. The system of claim 4 wherein said first threshold is higher when it is lower humidity than when it is higher humidity.

6. The system of claim 1 wherein said first environmental characteristic is sunlight.

7. The system of claim 6 wherein said first threshold is higher when it is night than when it is day.

8. The system of claim 1 wherein said first environmental characteristic is wind speed.

9. The system of claim 8 wherein said first threshold is higher when it is windy than when it is not windy.

10. The system of claim 1 further comprising a second environmental sensor for monitoring a second environmental characteristic;
    wherein said first threshold changes and is based on said first environmental characteristic and on said second environmental characteristic.

11. The system of claim 1 further comprising:
    a second hazardous material sensor for measuring the amount of a second hazardous material; and
    a second alarm that is issued when the amount of said second hazardous material reaches a second threshold, wherein said second threshold changes and is based on said first environmental characteristic.

12. A method comprising:
    monitoring a first environmental characteristic;
    measuring the amount of a first hazardous material; and
    issuing a first alarm when the amount of said first hazardous material reaches a first threshold, wherein said first threshold changes and is based on said first environmental characteristic.

13. The method of claim 12 wherein said first environmental characteristic is precipitation.

14. The method of claim 13 wherein said first threshold is higher when it is precipitating than when it is not precipitating.

15. The method of claim 12 wherein said first environmental characteristic is humidity.

16. The method of claim 15 wherein said first threshold is higher when it is lower humidity than when it is higher humidity.

17. The method of claim 12 wherein said first environmental characteristic is sunlight.

18. The method of claim 17 wherein said first threshold is higher when it is night than when it is day.

19. The method of claim 12 wherein said first environmental characteristic is wind speed.

20. The method of claim 19 wherein said first threshold is higher when it is windy than when it is not windy.

21. The method of claim 12 further comprising:
    monitoring a second environmental characteristic;
    wherein said first threshold changes and is based on said first environmental characteristic and on said second environmental characteristic.

22. The method of claim 12 further comprising:
    measuring the amount of a second hazardous material; and
    issuing a second alarm when the amount of said second hazardous material reaches a second threshold, wherein said second threshold changes and is based on said first environmental characteristic.

* * * * *